(12) United States Patent
Shibata

(10) Patent No.: US 11,327,049 B2
(45) Date of Patent: May 10, 2022

(54) ULTRASONIC APPARATUS, AND PROGRAM FOR CONTROLLING THE SAME

(71) Applicant: General Electric Company, Schenectady, NY (US)

(72) Inventor: Yuko Shibata, Tokyo (JP)

(73) Assignee: General Electric Company, Schenectady, NY (US)

( * ) Notice: Subject to any disclaimer, the term of this patent is extended or adjusted under 35 U.S.C. 154(b) by 462 days.

(21) Appl. No.: 16/658,440

(22) Filed: Oct. 21, 2019

(65) Prior Publication Data

US 2020/0132634 A1   Apr. 30, 2020

(30) Foreign Application Priority Data

Oct. 24, 2018 (JP) ............... JP2018-199810

(51) Int. Cl.
*A61B 8/08* (2006.01)
*A61B 8/00* (2006.01)
*G01N 29/04* (2006.01)

(52) U.S. Cl.
CPC .......... *G01N 29/043* (2013.01); *A61B 8/462* (2013.01); *A61B 8/485* (2013.01); *A61B 8/52* (2013.01); *G01N 2291/02466* (2013.01)

(58) Field of Classification Search
CPC ........ G01N 2291/02466; G01N 29/043; A61B 8/08; A61B 8/54; A61B 8/52; A61B 8/462; A61B 8/5246; A61B 8/485; A61B 8/5215; A61B 8/4444
USPC .......................................................... 73/1.82
See application file for complete search history.

(56) References Cited

U.S. PATENT DOCUMENTS

| 8,500,639 B2 * | 8/2013 | Yao .......................... A61B 8/08 600/437 |
| 9,351,707 B2 * | 5/2016 | Tamura ............... G01S 15/8979 |
| 2013/0218011 A1 | 8/2013 | Benson |

(Continued)

FOREIGN PATENT DOCUMENTS

| JP | 2007312958 A | 12/2007 |
| JP | 2015058193 A | 3/2015 |

OTHER PUBLICATIONS

Japanese Application No. 2018-199810 filed Oct. 24, 2018—Notice of Preliminary Rejection dated Jul. 14, 2020; 10 pages.

(Continued)

*Primary Examiner* — Jacques M Saint Surin

(57) ABSTRACT

[Problem] To provide an ultrasonic apparatus that enables one to find a factor that lowers reliability of a measurement value relating to elasticity of biological tissue.
[Means for Solution] An ultrasonic diagnostic apparatus comprises a control circuit executing: a measurement-value calculating function 535 of calculating a measurement value relating to elasticity of the biological tissue based on echo signals from ultrasonic detecting pulses; an index-value calculating function 536 of calculating an index value indicating a degree of reliability for the measurement value for each of a plurality of factors that deteriorate the reliability of the measurement value based on the echo signals from the ultrasonic detecting pulses; and a notifying function of notifying a factor corresponding to at least one index value for which the degree of reliability does not meet a required standard.

18 Claims, 12 Drawing Sheets

(56) References Cited

U.S. PATENT DOCUMENTS

| | | |
|---|---|---|
| 2015/0119712 A1* | 4/2015 | Tanigawa ............ G01S 7/52085 |
| | | 600/438 |
| 2015/0173720 A1 | 6/2015 | Yoshikawa |
| 2015/0342566 A1* | 12/2015 | Matsumoto ............ A61B 8/485 |
| | | 600/438 |
| 2016/0183926 A1 | 6/2016 | Asami |
| 2016/0249884 A1* | 9/2016 | Hashimoto ............ A61B 8/485 |
| | | 600/438 |
| 2016/0345939 A1 | 12/2016 | Toji |
| 2017/0245832 A1 | 8/2017 | Kawata |

OTHER PUBLICATIONS

Japanese Application No. 2018-199810 filed Oct. 24, 2018—Notice of Allowance dated Oct. 6, 2020; 4 pages.

\* cited by examiner

ULTRASONIC APPARATUS, AND PROGRAM FOR CONTROLLING THE SAME

FIELD OF THE INVENTION

The present invention relates to an ultrasonic apparatus for detecting shear waves generated in biological tissue by push pulses to calculate a measurement value relating to elasticity of the biological tissue, and to a program for controlling the same.

BACKGROUND

Among ultrasonic diagnostic apparatuses as an example of an ultrasonic apparatus, an apparatus for measuring elasticity of biological tissue is commonly known. Techniques of calculating a value relating to elasticity of biological tissue include one involving transmitting ultrasonic pulses having a high sound pressure, i.e., push pulses, to the biological tissue from an ultrasonic probe. This technique detects by ultrasonic detecting pulses a displacement of the biological tissue caused by the push pulses in the biological tissue. Based on the detection, a velocity of propagation of the shear waves is then calculated as the measurement value relating to elasticity of the biological tissue. The ultrasonic diagnostic apparatus displays the calculated measurement value as a numeric value or displays an elasticity image according to the measurement value.

However, a measurement value that does not accurately reflect elasticity of the biological tissue is sometimes obtained. In spite of such a fact that a measurement value with low reliability may be sometimes obtained, when only such a measurement value or an elasticity image is just displayed, a user cannot judge whether to accept the measurement value or not. Accordingly, there have been an ultrasonic diagnostic apparatus that, when a measurement value with low reliability is obtained, suppresses display of the measurement value or elasticity image, an ultrasonic diagnostic apparatus that displays an index of reliability, and the like (see Patent Document 1, for example).

PRIOR-ART REFERENCE

Patent Document

[Patent Document 1] Japanese Patent No. 6169707

SUMMARY OF THE INVENTION

Problem to be Solved by the Invention

When a user recognizes that a measurement value with low reliability has been obtained, (s)he needs to perform the measurement again. However, there may be a plurality of factors considered to lower reliability of the measurement value. For example, such factors may include the following ones: a region of interest for elasticity measurement is a region containing liquid, such as a cyst or blood, as a main component; motion of an ultrasonic probe or body motion of a subject to be examined is too large to detect a shear wave-induced displacement of biological tissue; a region of interest is so deep that an SN ratio in echo signals from ultrasonic detecting pulses is poor; and a region of interest is too rigid to generate sufficient shear waves.

Since there are such a plurality of factors, in the case that a measurement value with low reliability is obtained, mere inhibition of display of such a measurement value or an elasticity image or mere display of an index of reliability does not allow a user to find what factor causes such low reliability. Therefore, the user has no idea what to do for eliminating a factor that deteriorates reliability of the measurement value. The user is thus required to repeat measurement by trial and error, which sometimes results in an elongated examination time.

Means for Solving the Problem

The invention, in one aspect, made for solving the aforementioned problem is an ultrasonic apparatus comprising: an ultrasonic probe for performing transmission of ultrasonic push pulses to biological tissue in a subject to be examined, and transmission of ultrasonic detecting pulses for detecting shear waves generated by said push pulses in said biological tissue; and a control circuit, wherein said control circuit executes: a measurement-value calculating function of calculating a measurement value relating to elasticity of said biological tissue based on echo signals from said ultrasonic detecting pulses; an index-value calculating function of calculating an index value indicating a degree of reliability of said measurement value for each of a plurality of factors that deteriorate the reliability of said measurement value based on the echo signals from the ultrasonic detecting pulses; and a notifying function of notifying a factor corresponding to at least one index value for which said degree of reliability does not meet a required standard.

Effect of the Invention

According to the invention in the aspect described above, a factor corresponding to an index value for which the degree of reliability does not meet a required standard is notified by said notifying function, so that a user of the ultrasonic apparatus can find a factor that lowers reliability of the measurement value.

MODES FOR CARRYING OUT THE INVENTION

Now embodiments of the present invention will be described. The following description will be made on an ultrasonic diagnostic apparatus for displaying an ultrasonic image of a subject to be examined for the purpose of diagnosis, etc., as an example of the ultrasonic apparatus in accordance with the present invention.

Figure 1:
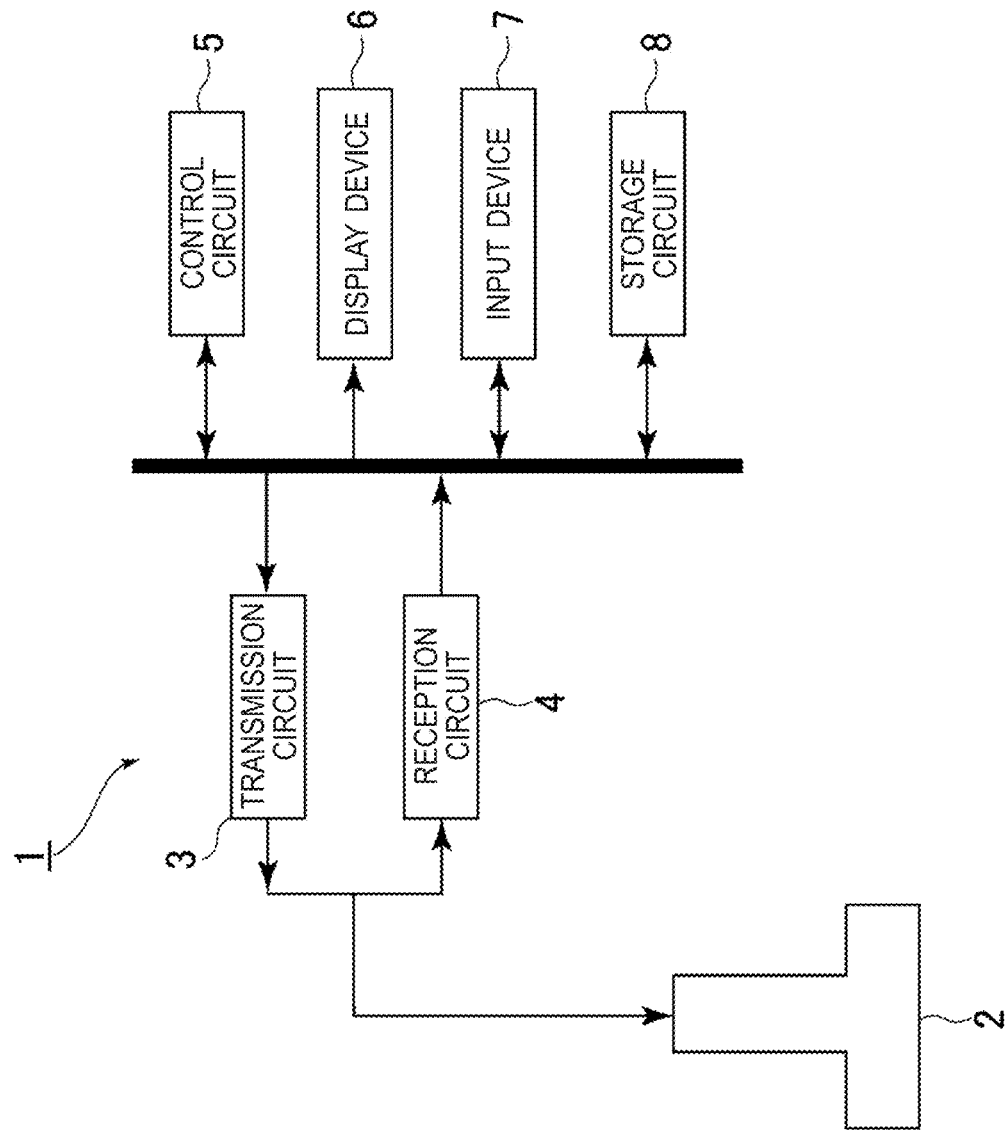
FIG. 1 A block diagram showing an exemplary ultrasonic diagnostic apparatus in an embodiment.

An ultrasonic diagnostic apparatus 1 shown in FIG. 1 comprises an ultrasonic probe 2, a transmission circuit 3, a reception circuit 4, a control circuit 5, a display device 6, an input device 7, and a storage circuit 8. The ultrasonic diagnostic apparatus 1 has a configuration as a computer.

The ultrasonic probe 2 has ultrasonic transducers (not shown) in which ultrasound is transmitted to biological tissue in a subject to be examined, and echo signals therefrom are received. By the ultrasonic probe 2, ultrasonic pulses (push pulses) for generating shear waves in the biological tissue are transmitted. Moreover, by the ultrasonic probe 2, ultrasonic detecting pulses for detecting the shear waves generated by the push pulses in the biological tissue are transmitted, and echo signals therefrom are received. The ultrasonic probe 2 is an exemplary embodiment of the ultrasonic probe in the present invention.

Moreover, by the ultrasonic probe 2, ultrasonic B-mode imaging pulses for producing a B-mode image are transmitted, and echo signals therefrom are received.

The transmission circuit 3 controls ultrasound transmission by the ultrasonic probe 2. Specifically, the transmission circuit 3 drives the ultrasonic probe 2 based on control signals from the control circuit 5 to transmit the aforementioned several kinds of ultrasonic pulses having predetermined transmission parameters.

The reception circuit 4 performs signal processing, such as phased-addition processing, on echo signals from ultrasound transmitted to the subject from the ultrasonic probe 2, reflected in the inside of the subject, and received at the ultrasonic probe 2. The reception circuit 4 performs signal processing based on a control signal from the control circuit 5.

The transmission circuit 3 and reception circuit 4 may be constructed from hardware. However, instead of the configuration comprising such transmission circuit 3 and reception circuit 4 as hardware, the ultrasonic diagnostic apparatus 1 may be configured to implement functions of the transmission circuit 3 and reception circuit 4 by software. That is, the apparatus 1 may be configured such that the control circuit 5 loads programs stored in the storage circuit 8 and executes the aforementioned functions of the transmission circuit 3 and reception circuit 4.

The control circuit 5 controls several sections in the ultrasonic diagnostic apparatus to perform several kinds of signal processing, image processing, and the like. The control circuit 5 may include one or more processors, for example. Optionally, the control circuit 5 may include a central processor unit (CPU), one or more microprocessors, graphic processor units (GPU), or any other electronic components capable of processing input data following specific logic instructions. The control circuit 5 is capable of loading a program stored in the storage circuit 8 to execute its instructions. The storage circuit 8 here is a tangible non-transitory computer-readable medium, which will be discussed later.

Figure 2:
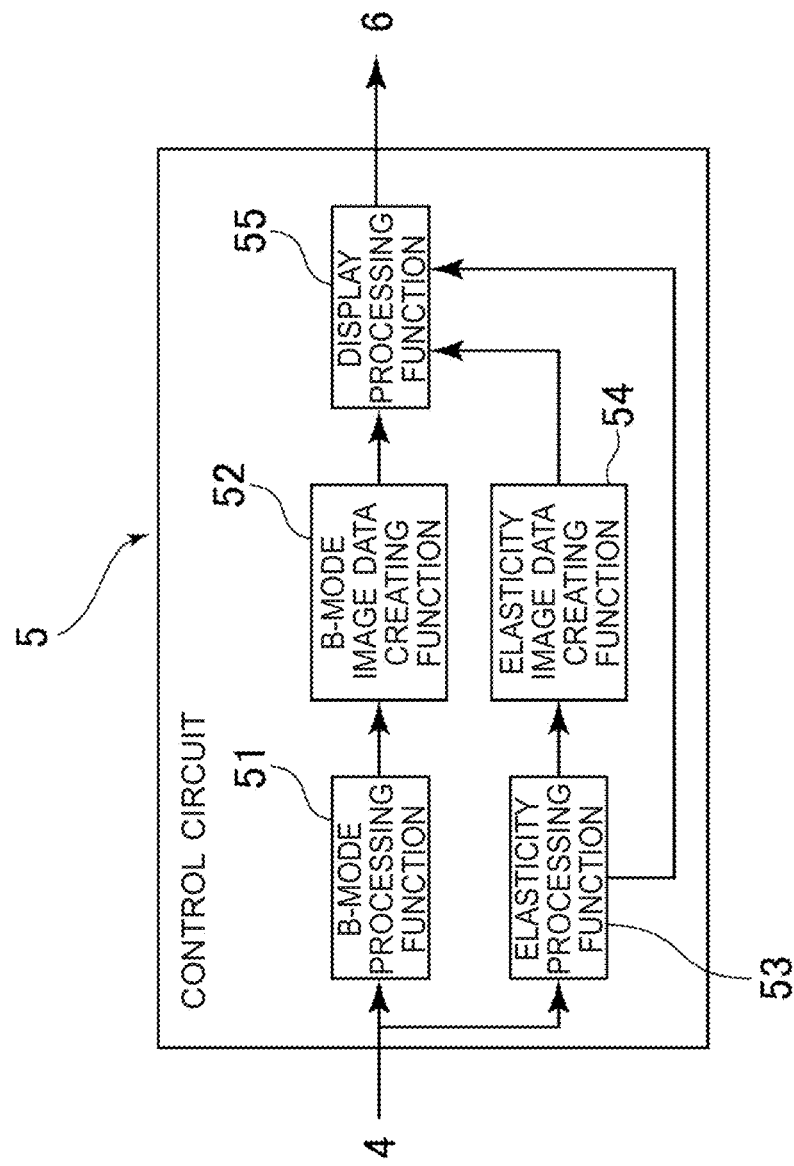
FIG. 2 An exemplary functional block diagram of a control circuit in the ultrasonic diagnostic apparatus in the embodiment.

FIG. 2 is an exemplary functional block diagram of the control circuit 5. The control circuit 5 executes a B-mode processing function 51, a B-mode image data creating function 52, an elasticity processing function 53, an elasticity image data creating function 54, and a display processing function 55. The control circuit 5 loads programs from the storage circuit 8, and executes these functions. While the control circuit 5 is shown in FIG. 2 as a functional block diagram, it may be configured as a complex of circuits and/or software modules. The control circuit 5 may also be implemented using any combination of a dedicated hardware board, a DSP (Digital Signal Processor), one or more processors, FPGAs (Field Programmable Gate Arrays), ASICs (Application Specific Integrated Circuits), and/or a tangible non-transitory computer-readable medium configured to issue commands to one or more processors. The control circuit 5 is an exemplary embodiment of the control circuit in the present invention.

The B-mode processing function 51 is a function of performing B-mode processing including logarithmic compression processing, envelope detection processing, etc. on echo data output from the reception circuit 4 to create B-mode data.

The B-mode image data creating function 52 is a function of scan-converting the B-mode data by a scan converter to create B-mode image data.

The elasticity processing function 53 is a function of performing signal processing of creating elasticity data relating to elasticity of biological tissue. The elasticity processing function 53 will be discussed later based on FIG. 3.

The elasticity image data creating function 54 scan-converts the elasticity data created by the elasticity processing function 53 by a scan converter to create elasticity image data, as will be discussed later. The elasticity image data creating function 54 creates the elasticity image data regarding a required region R (described below) defined in a B-mode image.

Figure 4:
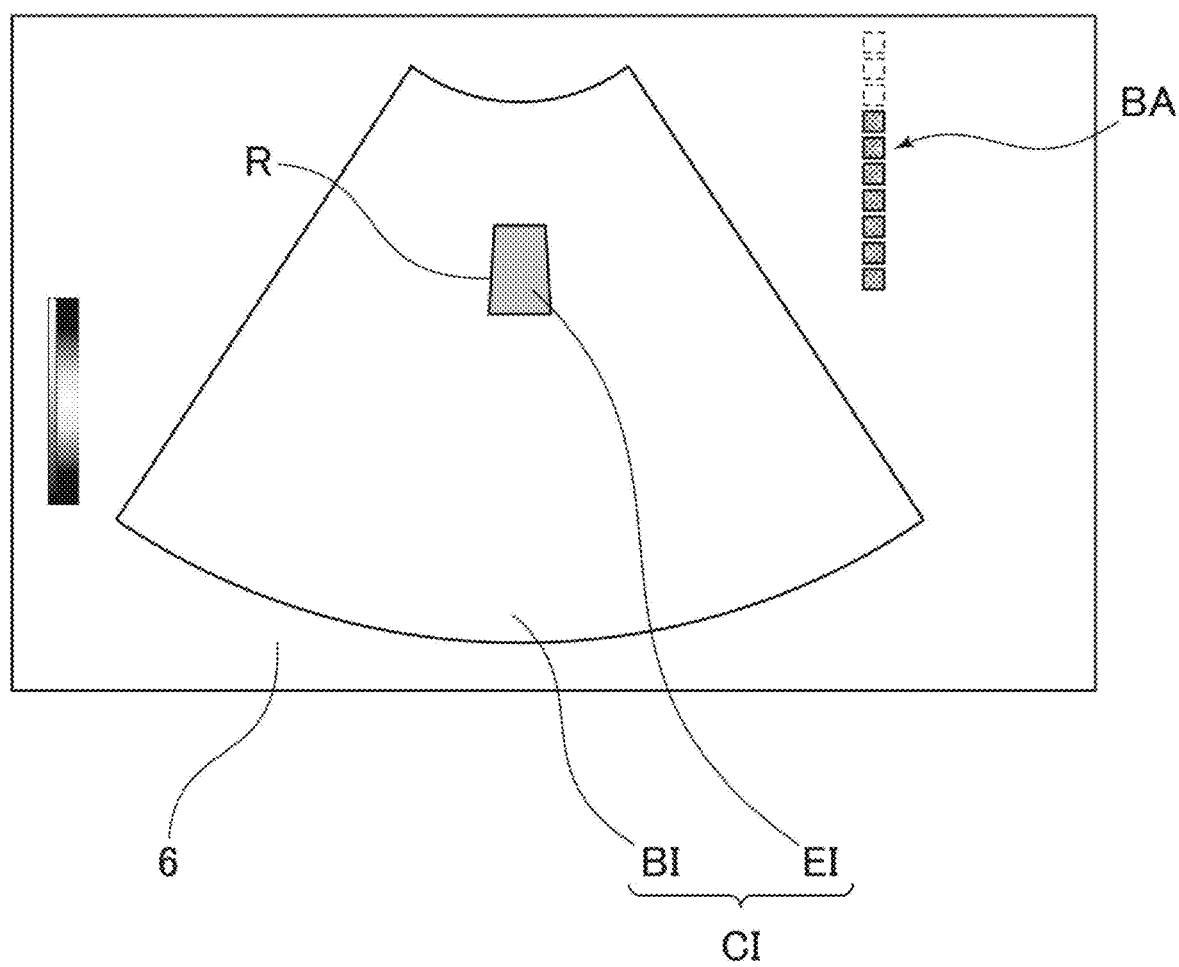
FIG. 4 A diagram showing an exemplary screen of a display device.

The display processing function 55 combines the B-mode image data and elasticity image data to produce combined image data. The display processing function 55 also displays a combined image CI on the display device 6 based on the combined image data, as shown in FIG. 4. The combined image CI is an image having a B-mode image BI based on the B-mode image data and an elasticity image EI based on the elasticity image data. The display processing function 55 displays the elasticity image EI in the required region R defined in the B-mode image BI. The elasticity image EI is a semi-transparent color image through which the B-mode image BI in the background passes. The color image is an image having colors depending upon the velocity of propagation or upon the elasticity value described later, which image has colors depending upon the elasticity of biological tissue.

The display processing function 55 moreover displays a bar BA along with the combined image CI side by side on the display device 6. The bar BA has a required color. The bar BA will be discussed later. The display processing function 55 is an exemplary embodiment of the notifying function in the present invention. The bar BA is an exemplary embodiment of the figure in the present invention.

Figure 3:
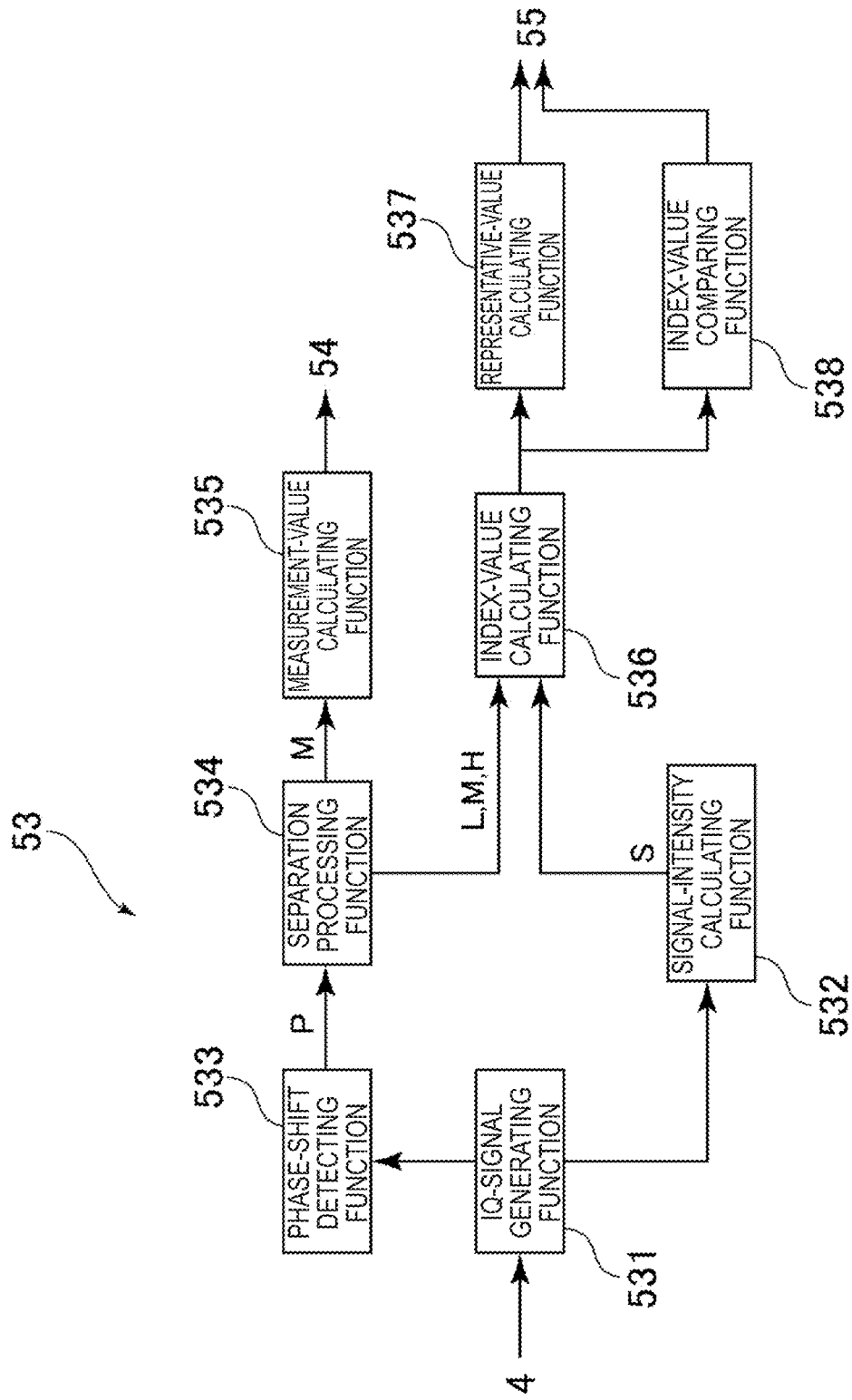
FIG. 3 A functional block diagram showing an example of details of an elasticity processing function.

Detailed functional blocks of the elasticity processing function 53 will now be described based on FIG. 3. As shown in FIG. 3, the elasticity processing function 53 comprises an IQ-signal generating function 531, a signal-intensity calculating function 532, a phase-shift detecting function 533, a separation processing function 534, a measurement-value calculating function 535, an index-value calculating function 536, a representative-value calculating function 537, and an index-value comparing function 538.

The IQ-signal generating function 531 is a function of performing quadrature detection processing on echo data (RF signals) output from the reception circuit 4 to generate an IQ signal. The IQ signal is subjected to processing by the signal-intensity detecting function 532 and phase-shift detecting function 533. The IQ-signal generating function 531 is an exemplary embodiment of the IQ signal generation in the present invention.

The signal-intensity calculating function 532 is a function of detecting signal intensity of echo signals from ultrasonic detecting pulses. In the present embodiment, the signal-intensity calculating function 532 calculates intensity of the IQ signal as the signal intensity of the echo signals. Specifically, the signal-intensity calculating function 532 calculates a sum S according to the following equation:

$$S=(I^2+Q^2)^{\wedge}(1/2) \quad \text{[Equation 1]}$$

The sum S calculated by the signal-intensity calculating function 532 is subjected to processing by the index-value calculating function 536. The signal-intensity calculating function 532 is an exemplary embodiment of the signal-intensity calculating function in the present invention.

The phase-shift detecting function 533 is a function of calculating a phase shift P in the echo signals by performing processing similar to color Doppler processing. Specifically, the phase-shift detecting function 533 performs autocorrelation processing on the IQ signal input from the IQ-signal generating function 531 to thereby detect a phase shift P in the echo signals. The phase shift P detected by the phase-shift detecting function 533 is subjected to processing by the separation processing function 534. The phase-shift detecting function 533 is an exemplary embodiment of the phase-shift detecting function in the present invention.

The separation processing function 534 is a function of separating a signal representing the phase shift P detected by the phase-shift detecting function 533 into a signal component in each of a plurality of frequency bands. The separation processing function 534 performs filter processing, for example, to separate the IQ signal into a signal component L in a low-frequency band, which is a frequency band lower than a frequency f1, a signal component M in a medium-frequency band of the frequency f1 or higher and lower than a frequency f2 (f2>f1), and a signal component H in a high-frequency band of the frequency f2 or higher. The signal component L in the low-frequency band, the signal component M in the medium-frequency band, and the signal component H in the high-frequency band obtained by the separation processing function 534 are subjected to processing by the index-value calculating function 536. The signal component M in the medium-frequency band is also subjected to processing by the measurement-value calculating function 535. The separation processing function 534 is an exemplary embodiment of the separation processing function in the present invention.

The measurement-value calculating function 535 is a function of calculating a measurement value V relating to elasticity of biological tissue based on the signal component M in the medium-frequency band obtained by the separation processing function 534. The measurement-value calculating function 535 calculates the measurement value V by detecting a temporal change of a displacement D of biological tissue caused by shear waves based on the signal component M in the medium-frequency band. The detection of the temporal change of the displacement D means detection of shear waves. Therefore, it may be said that the measurement-value calculating function 535 calculates the measurement value V relating to elasticity of the biological tissue based on the detected shear waves.

The measurement-value calculating function 535 calculates a velocity of propagation of shear waves according to a commonly known technique, for example, as the measurement value V. The velocity of propagation is obtained on a portion-by-portion basis, which portion corresponds to each of a plurality of points in a region corresponding to the required region R in the biological tissue, i.e., to each of pixels in the elasticity image EI.

The calculation of a velocity of propagation of shear waves will now be described in more detail. The displacement D is detected in each of a plurality of acoustic lines. The measurement-value calculating function 535 arithmetically calculates a velocity of propagation of shear waves in each of portions corresponding to a pixel based on a phase difference in waveforms of temporal changes of displacements D in two acoustic lines.

Data representing the velocity of propagation will be referred to herein as elasticity data. The measurement-value calculating function 535 may arithmetically calculate an elasticity value (Young's modulus (in Pa: pascal) of the biological tissue based on the velocity of propagation. In this case, the elasticity data may be data representing elasticity values. The elasticity data is subjected to processing by the elasticity image data creating function 54. The measurement-value calculating function 535 is an exemplary embodiment of the measurement-value calculating function in the present invention.

The index-value calculating function 536 is a function of calculating an index value I indicating a degree of reliability of the measurement value V for each of a plurality of factors that deteriorate reliability of the measurement value V. To calculate the index value I, the index-value calculating function 536 uses signals obtained by processing the echo signals from the ultrasonic detecting pulses. Specifically, the index-value calculating function 536 detects a temporal change of a displacement D of the biological tissue caused by shear waves based on the signal component M in the medium-frequency band obtained by the separation processing function 534. The index-value calculating function 536 calculates each of a plurality of the index values I based on at least one of the temporal change of the displacement D and the sum S obtained by the signal-intensity calculating function 532. Details thereof will be discussed later.

The index value I obtained by the index-value calculating function 536 is subjected to processing by the representative-value calculating function 537 and index-value comparing function 538. The index-value calculating function 536 is an exemplary embodiment of the index-value calculating function in the present invention.

The representative-value calculating function 537 is a function of calculating a representative value Ir of the index values indicating the degree of reliability of the measurement value V based on the plurality of index values I. Details thereof will be discussed later. The representative value Ir obtained by the representative-value calculating function 537 is subjected to processing by the display processing function 55. The representative-value calculating function 537 is an exemplary embodiment of the representative-value calculating function in the present invention.

The index-value comparing function 538 is a function of comparing the plurality of index values I to identify an index value $I_L$ that gives lowest reliability. The identified index value I is subjected to processing by the display processing function 55. The index comparing function 538 is an exemplary embodiment of the index-value comparing function in the present invention.

Returning to FIG. 1, the display device 6 is an LCD (Liquid Crystal Display), an organic EL (Electro-Luminescence) display, or the like.

The input device 7 is a device for accepting an input of a command, an input of information, and the like by an operator. The input device 7 is configured to comprise buttons, a keyboard, and the like for accepting the operator's inputs of a command and/or information, and to further comprise a pointing device, such as a trackball, and/or the like. Note that the buttons may include soft keys displayed on the display device 6, as well as hard keys. The input device 7 may also comprise a touch panel. In this case, the buttons include soft keys displayed on the touch panel.

The storage circuit 8 may be a tangible non-transitory or transitory computer-readable medium, including flash memory, a hard disk, RAM, ROM, and/or EEPROM. The storage circuit 8 may be used to store acquired B-mode data, B-mode image data, and color image data that are not scheduled to be instantly displayed, and other text and figures to be displayed on the display device 6, as well as other data.

The storage circuit 8 may also be used to store firmware or software corresponding, for example, to graphical user interface, one or more default image display settings, and/or programmed commands (those for the control circuit 5, for example).

Next, an operation of the ultrasonic diagnostic apparatus 1 in the present embodiment will be described. When the ultrasonic probe 2 has performed transmission/reception for ultrasonic B-mode imaging pulses, the B-mode processing function 51 creates B-mode data, and the B-mode image data creating function 52 creates B-mode image data. Moreover, when the ultrasonic probe 2 has performed transmission of push pulses and transmission/reception for ultrasonic detecting pulses, the measurement-value calculating function 535 in the elasticity processing function 53 calculates a measurement value V, and the elasticity image data creating function 54 creates elasticity image data.

Once the B-mode image data and elasticity image data have been created, the display processing function 55 displays a combined image CI having a B-mode image BI and an elasticity image EI on the display device 6, as shown in FIG. 4. The display processing function 55 also displays a bar BA along with the combined image CI side by side on the display device 6.

Figure 5:
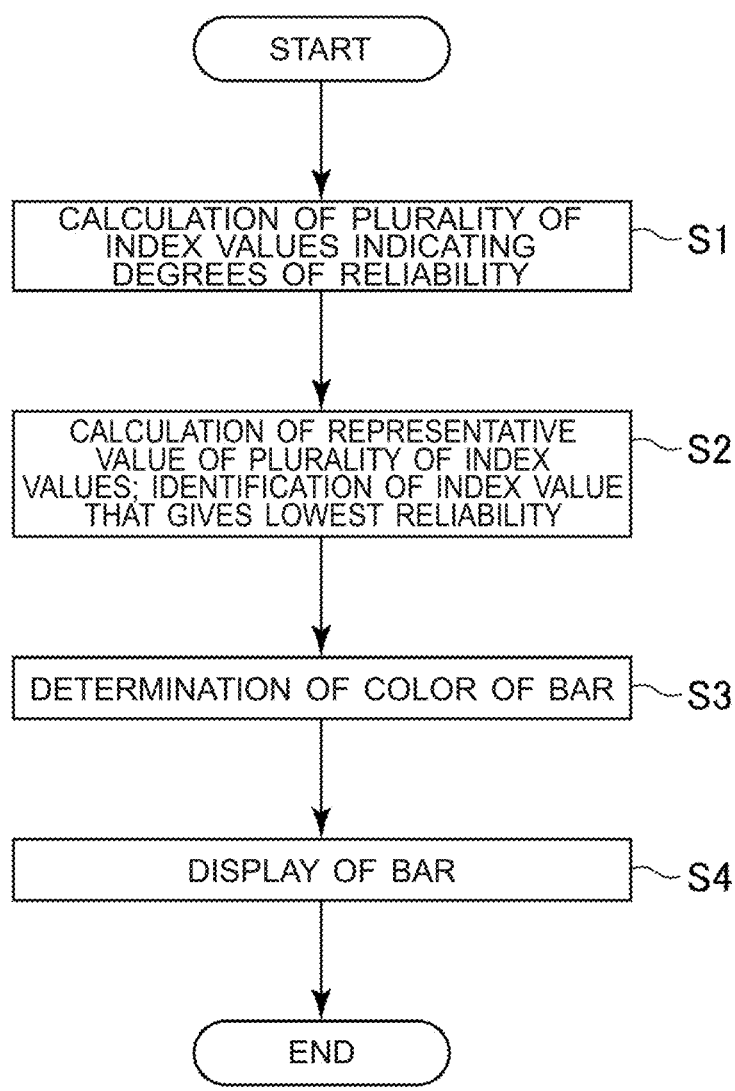
FIG. 5 A flow chart showing exemplary processing for displaying a bar in the ultrasonic diagnostic apparatus in the embodiment.

Display of the bar BA will now be described based on the flow chart in FIG. 5. First, at Step S1, the index-value calculating function 536 performs calculation of a plurality of index values I each indicating a degree of reliability of the measurement value V. In the present embodiment, the index-value calculating function 536 calculates a first index value I1, a second index value I2, a third index value I3, and a fourth index value I4 as the plurality of index values I. The index-value calculating function 536 calculates the first index value I1 to fourth index value I4 for each of points in every acoustic line corresponding to all pixels within the required region R.

The first index value I1 is an index value corresponding to one of factors that deteriorate reliability of the measurement value V, where the factor is that the position of the required region R defined in the B-mode image BI is too deep. To calculate the first index value I1, the index-value calculating function 536 calculates, for example, a ratio Rsn (SNR: Signal-to-Noise Ratio) between the sum S obtained by the signal-intensity calculating function 532 and a noise component. The noise component may be determined beforehand and stored in the storage circuit 8. Note that the smaller the ratio Rsn is, the lower the reliability of the measurement value V is by the factor that the position of the required region is too deep. The index-value calculating function 536 calculates a value of the ratio Rsn normalized into a range from 0 to 100% as the first index value I1. In the present embodiment, the normalization is applied so that a larger first index value I1 indicates higher reliability of the measurement value.

The second index value I2 is an index value corresponding to a factor of motion among factors that deteriorate reliability of the measurement value V, where the factor is that body motion of the subject occurs or the ultrasonic probe 2 moves. The index-value calculating function 536 detects the second index value I2 based on a temporal change of the displacement D of the biological tissue caused by shear waves. More specifically, the temporal change of the displacement D is a temporal change of the signal component M in the medium-frequency band obtained from the separation processing function 534. The index-value calculating function 536 calculates, for example, a correlation coefficient C indicating a degree of similarity between waveforms each representing a temporal change of the signal component M in the medium-frequency band at a certain point in adjacent acoustic lines. Note that the smaller the correlation coefficient C is, the lower the reliability of the measurement value V is by the factor of motion. The index-value calculating function 536 calculates a value of the correlation coefficient C normalized into a range from 0 to 100% as the second index value I2. In the present embodiment, the normalization is applied so that a larger second index value I2 indicates higher reliability of the measurement value.

The third index value I3 is an index value corresponding to one of factors that deteriorate reliability of the measurement value V, where the factor is that shear waves with magnitude sufficient to cause a displacement of the biological tissue are not generated. The index-value calculating function 536 detects the third index value I3 based on a temporal change of the displacement D of the biological tissue caused by shear waves. More specifically, the temporal change of the displacement D is, again, a temporal change of the signal component M in the medium-frequency band. The index-value calculating function 536 identifies, for example, an amplitude A in a waveform of the signal component M in the medium-frequency band. Note that the smaller the amplitude A is, the lower the reliability of the measurement value V is by the factor that shear waves with sufficient magnitude are not generated. The index-value calculating function 536 calculates a value of the amplitude A normalized into a range from 0 to 100% as the third index value I3. In the present embodiment, the normalization is applied so that a larger third index value I3 indicates higher reliability of the measurement value.

The fourth index value I4 is an index value corresponding to one of factors that deteriorate reliability of the measurement value V, where the factor is that a liquid component, such as blood flow or a cyst, exists in a path of propagation of shear waves, for example. The index-value calculating function 536 calculates, for example, a ratio Rp of a power (energy) of the signal component H in the high-frequency band to that of the signal component M in the medium-frequency band. Note that the larger the ratio Rp is, the lower the reliability of the measurement value V is by the factor that a liquid component exists. The index-value calculating function 536 calculates a value of the ratio Rp normalized into a range from 0 to 100% as the fourth index value I4. In the present embodiment, the normalization is applied so that a larger fourth index value I4 indicates higher reliability of the measurement value.

It should be noted that the calculation techniques for the first index value I1 to fourth index value I4 are exemplary, and they are not limited thereto.

Next, at Step S2, based on the first index value I1 to fourth index value I4 calculated for each of points in every acoustic line, the representative-value calculating function 537 calculates a representative value Ir of the index values in the required region R. For example, the representative-value calculating function 537 first calculates a representative value Irp of the first index value I1 to fourth index value I4 for each of points in every acoustic line corresponding to all pixels in the required region R. The representative-value calculating function 537 may calculate the representative value Irp for each point by multiplying the first index value I1 to fourth index value I4 obtained for each point with one another. Alternatively, the representative-value calculating function 537 may calculate an average of the first index value I1 to fourth index value I4 as the representative value Irp for each point.

Based on the representative value Irp for each point, the representative-value calculating function 537 calculates the representative value Ir of the index values in the required region R. For example, the representative-value calculating function 537 calculates for an average of the representative value Irp for each point as the representative value Ir.

It should be noted that the calculation technique for the representative value Ir described here is exemplary, and it is not limited thereto. For example, the representative-value calculating function 537 calculates a representative value I1r of the first index value I1, a representative value I2r of the second index value I2, a representative value I3r of the third index value I3, and a representative value I4r of the fourth index value I4 at each of points in every acoustic line in the required region R by multiplicative calculation, averaging calculation, or the like similarly to the above. The representative-value calculating function 537 may then apply averaging calculation to the four values including the representative value I1r of the first index value I1 to the representative value I4r of the fourth index value I4 to calculate the representative value Ir of the index values in the required region R.

Moreover, at Step S2, the index-value comparing function 538 compares the first index value I1 to fourth index value I4 with one another to identify an index value $I_L$ that gives lowest reliability.

Next, at Step S3, the display processing function 55 determines a color of the bar BA to be displayed on the display device 6. The display processing function 55 performs the determination of a color by deciding whether or not the representative value Ir meets a required standard stored in the storage circuit 8. In addition, in the case that the representative value Ir does not meet the required standard, the display processing function 55 determines a color depending upon the factor corresponding to the index value $I_L$ that gives lowest reliability.

The aforementioned determination of a color will now be more specifically described. For example, the required standard is that the representative value Ir is a threshold TH or larger. In this case, the display processing function 55 decides whether or not the representative value Ir is the threshold TH or larger. In the case that the representative value Ir is the threshold TH or larger, the display processing function 55 determines a required color CO1 as the color of the bar BA. In the case that the representative value Ir is less than the threshold TH, on the other hand, the display processing function 55 determines a different color depending upon the factor corresponding to the index value $I_L$ that gives lowest reliability as the color of the bar BA. For example, in the case that the representative value Ir is less than the threshold TH and the index value $I_L$ that gives lowest reliability is the first index value I1, a color CO2 is determined as the color of the bar BA. In the case that the representative value Ir is less than the threshold TH and the index value $I_L$ that gives lowest reliability is the second index value I2, a color CO3 is determined as the color of the bar BA. In the case that the representative value Ir is less than the threshold TH and the index value $I_L$ that gives lowest reliability is the third index value I3, a color CO4 is determined as the color of the bar BA. In the case that the representative value Ir is less than the threshold TH and the index value $I_L$ that gives lowest reliability is the fourth index value I4, a color CO5 is determined as the color of the bar BA. The colors CO1 to CO5 are mutually different colors, and are stored beforehand in the storage circuit 8. The colors CO1 to CO5 may be defined by a user, or may be configured to be changeable to a different color(s).

The threshold TH is stored in the storage circuit 8, and is set, for example, to a value considered to have questionable reliability of the measurement value V to a user. The threshold TH may be set beforehand, or may be configured to be changeable by a user.

Figure 6:
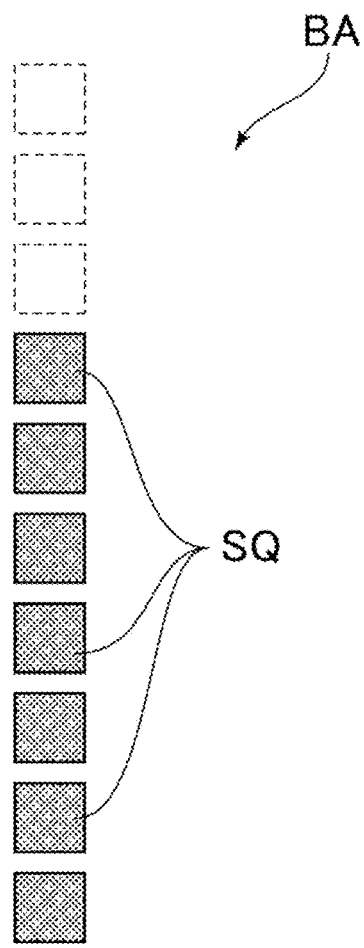
FIG. 6 An enlarged view showing an exemplary bar.
Figure 7:
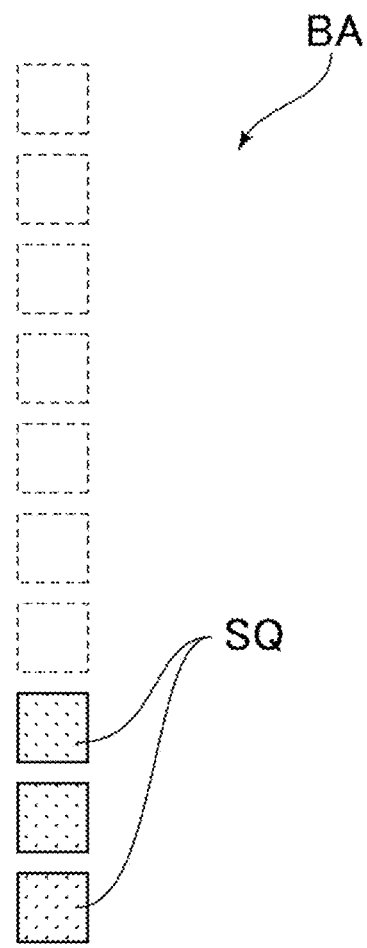
FIG. 7 An enlarged view showing the exemplary bar displayed in a shorter state than the length shown in FIG. 6.

Next, at Step S4, the display processing function 55 displays the bar BA on the display device 6 as shown in FIG. 4. The bar BA indicates the representative value Ir of the index values. The bar BA will now be described additionally referring to FIGS. 6 and 7. In the present embodiment, the bar BA is composed of rectangles SQ in a number depending upon the representative value Ir of the index values. More specifically, the larger the representative value Ir is, the larger the number of rectangles SQ composing the bar is (FIG. 6); and the smaller the representative value Ir is, the smaller the number of rectangles SQ composing the bar BA is (FIG. 7). Therefore, the bar BA has a length depending upon the representative value Ir. When a plurality of the rectangles SQ are to be displayed, the plurality of rectangles SQ are displayed in an arrangement in the vertical direction of the display device 6.

The bar BA in the present embodiment shown in the drawings has ten rectangles SQ at maximum with the intention of displaying the magnitude of the representative value Ir in ten levels. It should be noted that the number of levels is not limited to ten. Moreover, the bar BA is not limited to that composed of the rectangles SQ.

The bar BA has one of the colors CO1 to CO5. In other words, the rectangles SQ composing the bar BA have the one of the colors CO1 to CO5. In the drawings, the color is represented by dots. By the bar BA having one of the colors CO2 to CO5 being displayed, the user can find an index value $I_L$ that gives lowest reliability of the first index value I1 to fourth index value I4. This enables the user to identify a factor that deteriorates reliability of the measurement value V, and to find what to do to obtain a reliable measurement value V.

Moreover, when the bar BA having the color CO1 is displayed, the user can find that the measurement value V is a reliable value and the elasticity image EI is a reliable image.

The bar BA may be updated each time an elasticity image EI in one frame is obtained.

Figure 8:
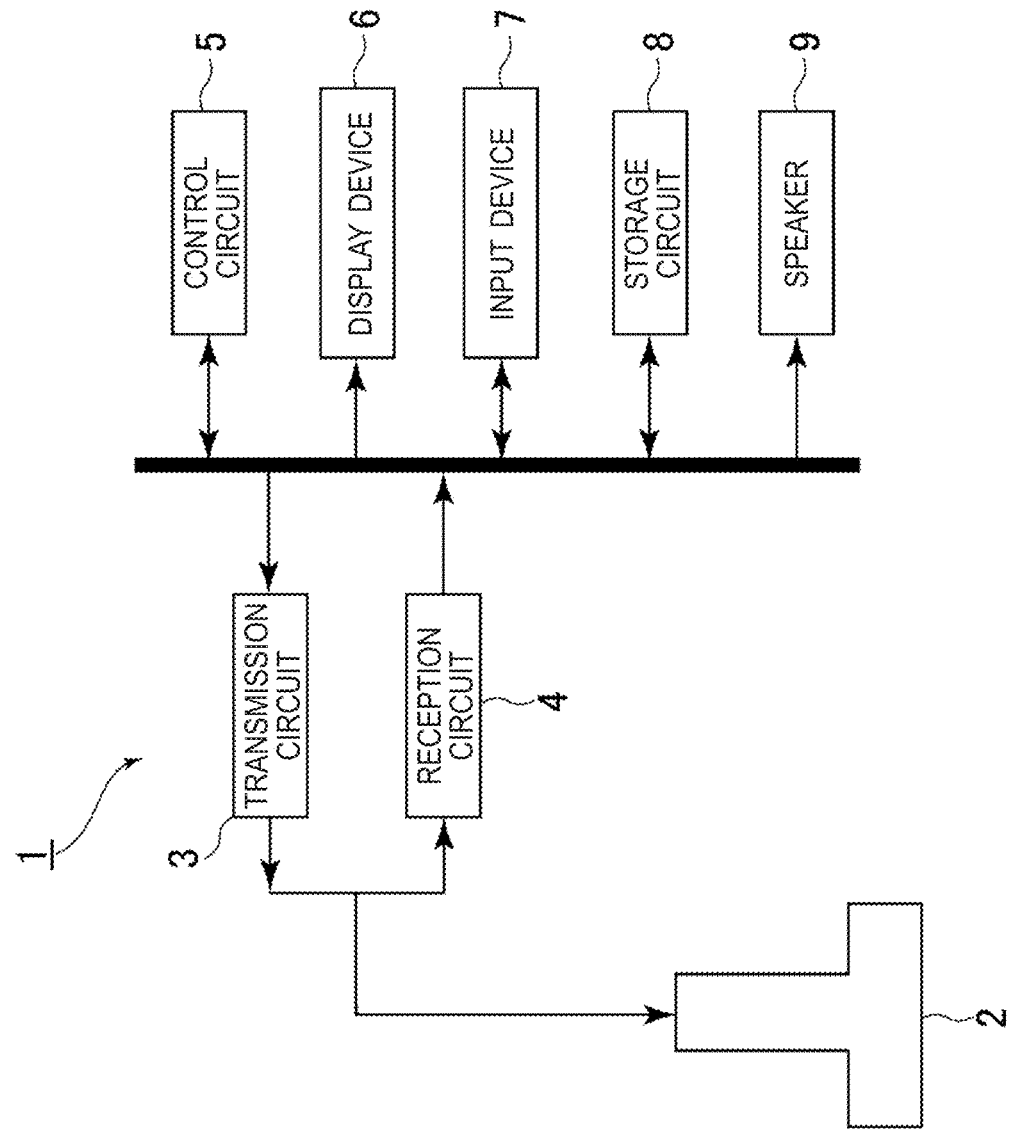
FIG. 8 A block diagram showing another exemplary ultrasonic diagnostic apparatus in an embodiment.

In the embodiment described above, the display processing function 55 may display measures to eliminate the factor corresponding to the index value $I_L$ that gives lowest reliability by text or the like on the display device 6. Moreover, in the case that the ultrasonic diagnostic apparatus 1 has a speaker 9 as shown in FIG. 8, the control circuit 5 may output the measures to eliminate the factor corresponding to the index value $I_L$ that gives lowest reliability by voice from the speaker 9. The measures to eliminate the factor corresponding to the index value $I_L$ that gives lowest reliability are stored beforehand in the storage circuit 8.

While the present invention has been described with reference to the embodiments above, it will be easily recognized that the present invention may be practiced with several modifications without departing from the spirit and scope thereof. For example, in the embodiments above, the bar BA is merely an example of the figure indicating the representative value Ir of the index values. The display processing function 55 may be configured to display a figure other than the bar BA to thereby indicate the representative value Ir. In this case, again, the figure indicating the representative value Ir is displayed in one of the colors CO1 to CO5, for example.

Moreover, the present invention is not limited to a configuration in which the representative value of the index values is indicated by displaying a figure. For example, the display processing function 55 may display text indicating the representative value Ir on the display device. In this case, again, the display processing function 55 displays the text in one of the colors CO1 to CO5, for example, to notify a factor corresponding to the index value $I_L$ that gives lowest reliability.

Furthermore, at least one of a figure and text indicating the representative value Ir of the index values may be displayed in a different display mode depending upon the factor corresponding to the index value $I_L$ that gives lowest reliability, and the present invention is not limited to a case in which the aforementioned figure and text are displayed in different colors.

In addition, the present invention is not limited to a case in which the factor corresponding to the index value $I_L$ that gives lowest reliability is notified by displaying at least one of a figure and text indicating the representative value. For example, the display processing function 55 may display text, a figure, or the like indicating the factor corresponding to the index value $I_L$ that gives lowest reliability on the display device 6.

Moreover, the factor corresponding to the index value $I_L$ that gives lowest reliability may be notified by a technique other than the figure and text. For example, the control circuit 5 may be configured to output the factor corresponding to the index value $I_L$ that gives lowest reliability by sound, such as voice, from the speaker 9.

Figure 9:
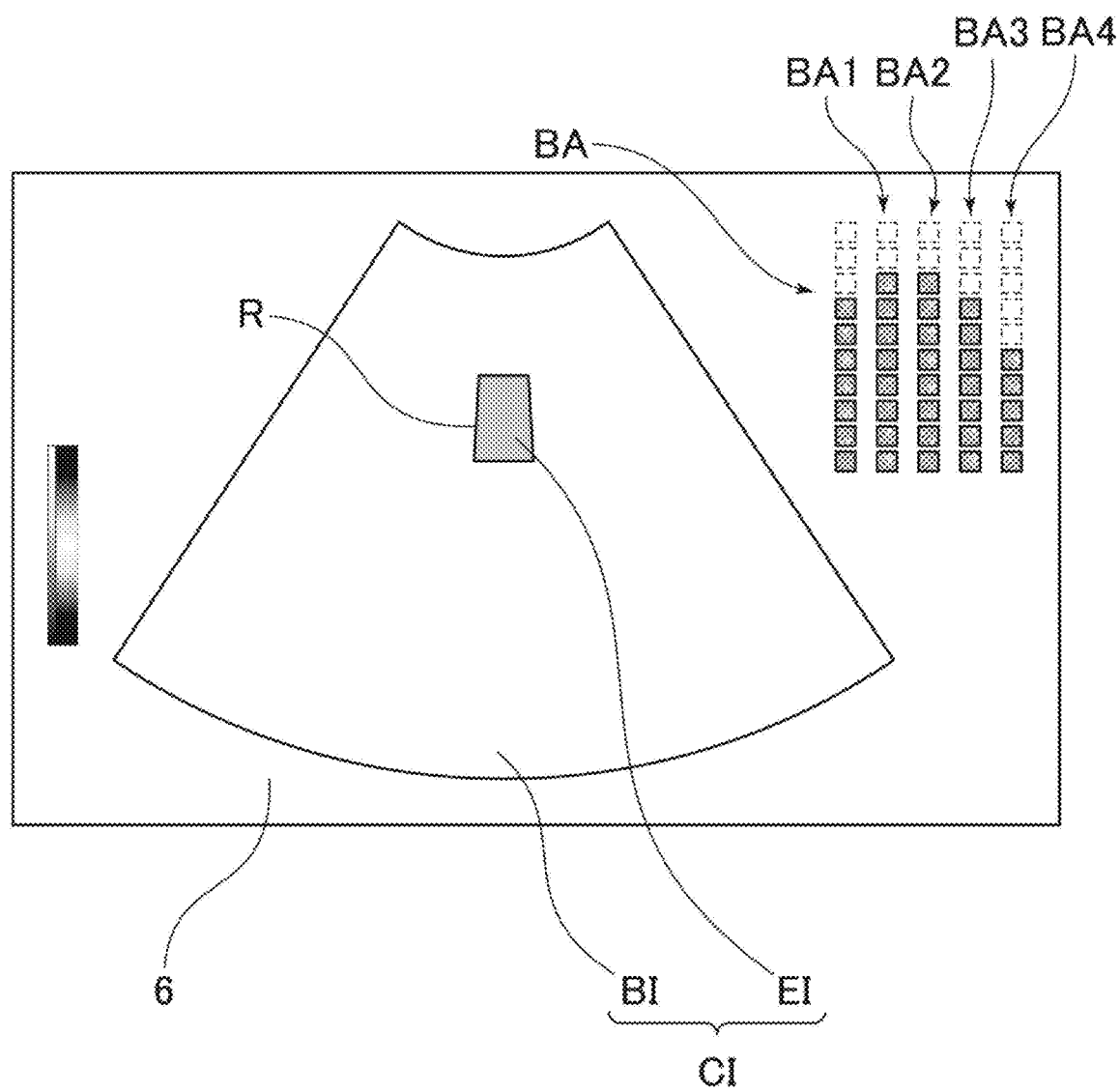
FIG. 9 A diagram showing another exemplary screen of the display device.
Figure 10:
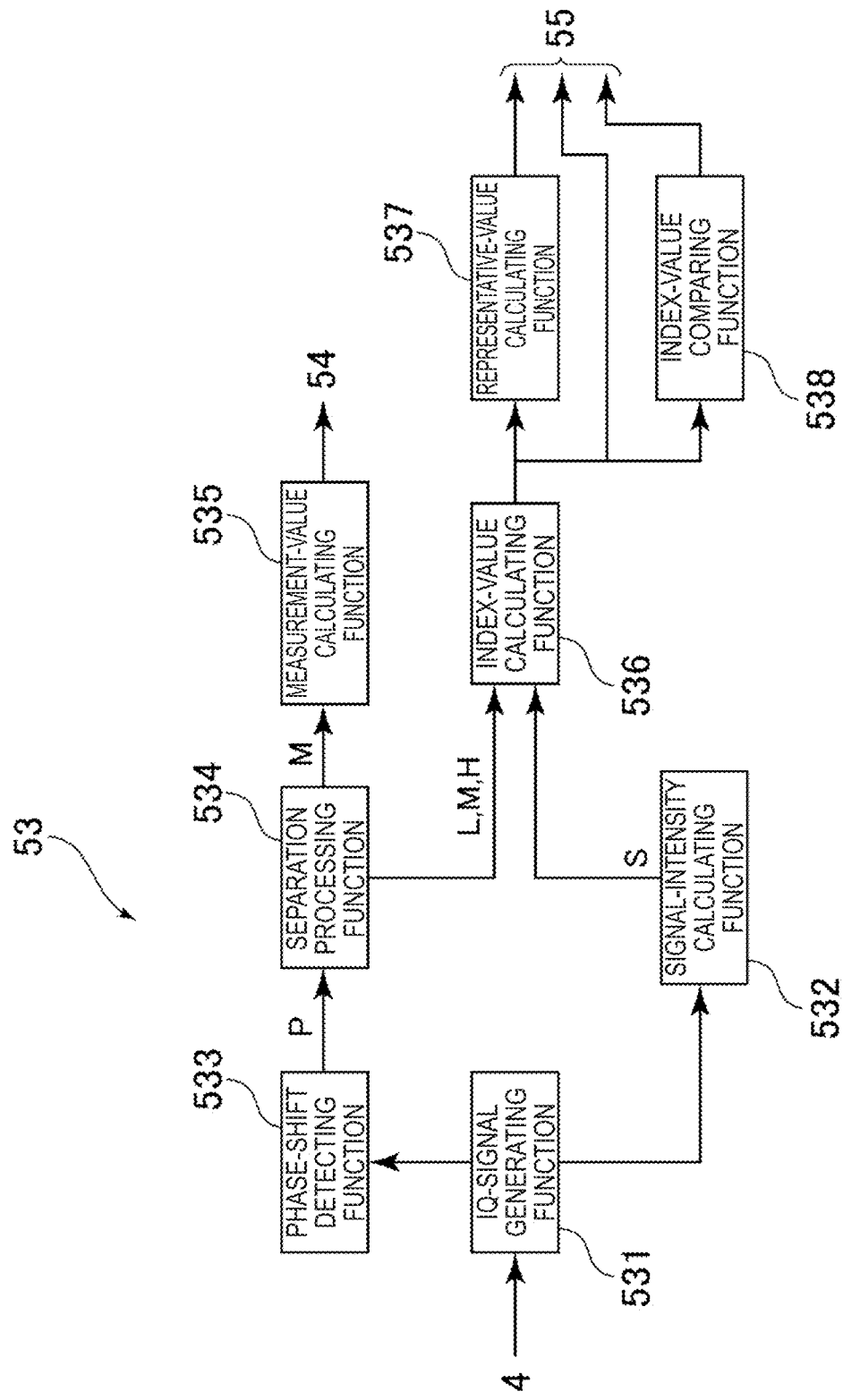
FIG. 10 A functional block diagram showing another example of details of the elasticity processing function.

Furthermore, as shown in FIG. 9, the display processing function 55 may display the bar BA indicating the representative value Ir on the display device 6 along with a first bar BA1 indicating the first index value I1, a second bar BA2 indicating the second index value I2, a third bar BA3 indicating the third index value I3, and a fourth bar BA4 indicating the fourth index value I4. In this case, as shown in FIG. 10, the first index value I1 to fourth index value I4 calculated by the index-value calculating function 536 are also subjected to processing by the display processing function 55, in addition to the representative-value calculating function 537 and index-value comparing function 538.

Similarly to the bar BA, the first bar BA1 to fourth bar BA4 have respective lengths depending upon the first index value I1 to fourth index value I4. Therefore, by the first bar BA1 to fourth bar BA4 being displayed, the user can find whether or not the first index value I1 to fourth index value I4 are the threshold TH described above or larger. This enables the user to find one of factors corresponding to the first index value I1 to fourth index value I4 that deteriorates reliability of the measurement value V. In the present embodiment, the act of displaying the first bar BA1 to fourth bar BA4 is equivalent to the act of notifying a factor corresponding to at least one index value for which the degree of reliability of the measurement value V does not meet a required standard.

The display processing function 55 may display the first bar BA1 to fourth bar BA4 in the same color or in different colors. Moreover, the display processing function 55 may switch the color of each of the first bar BA1 to fourth bar BA4 between a case in which the first index value I1 to fourth index value I4 are the threshold TH described above or larger and a case in which they are less than the threshold TH.

Figure 11:
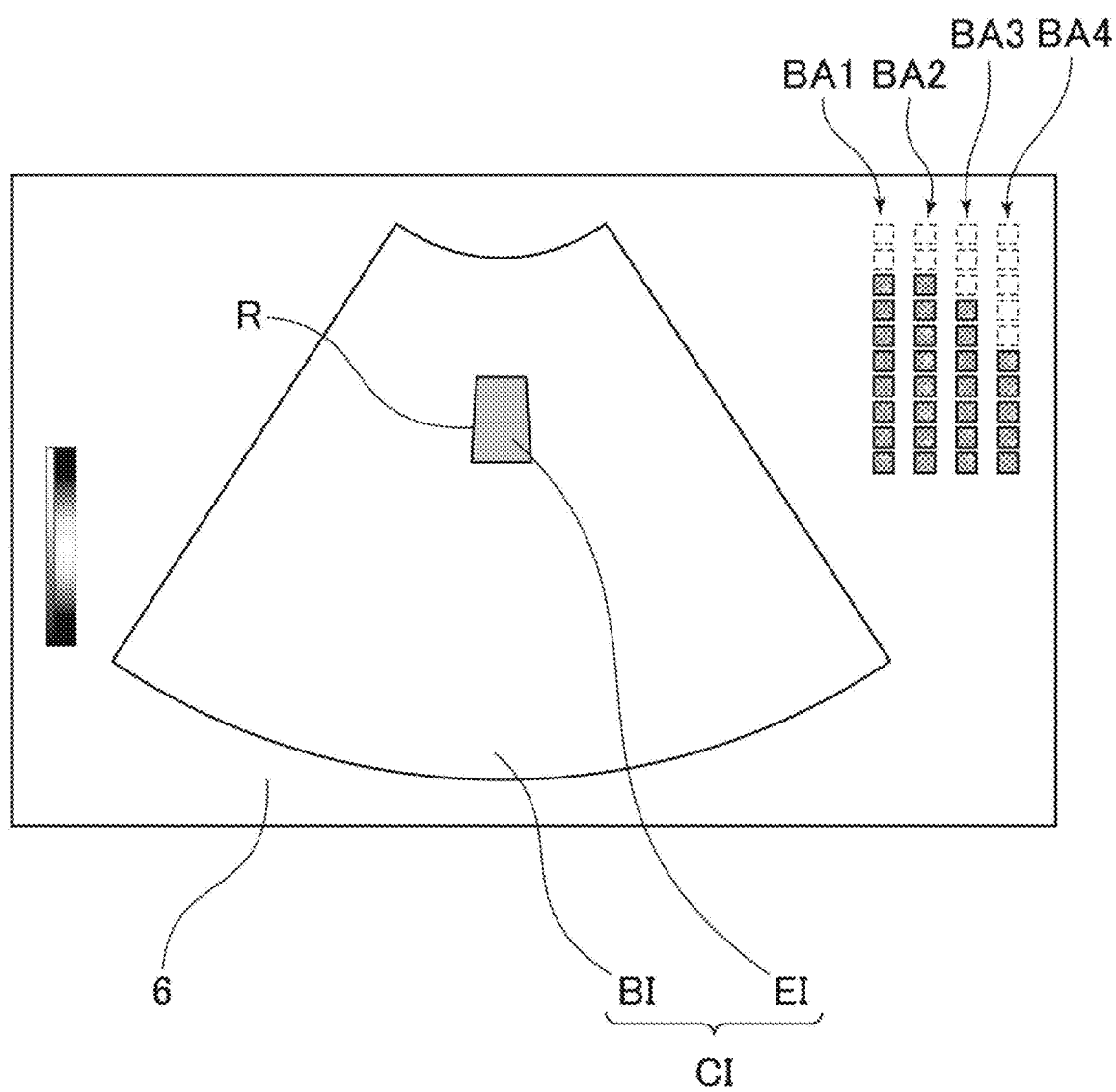
FIG. 11 A diagram showing another exemplary screen of the display device.
Figure 12:
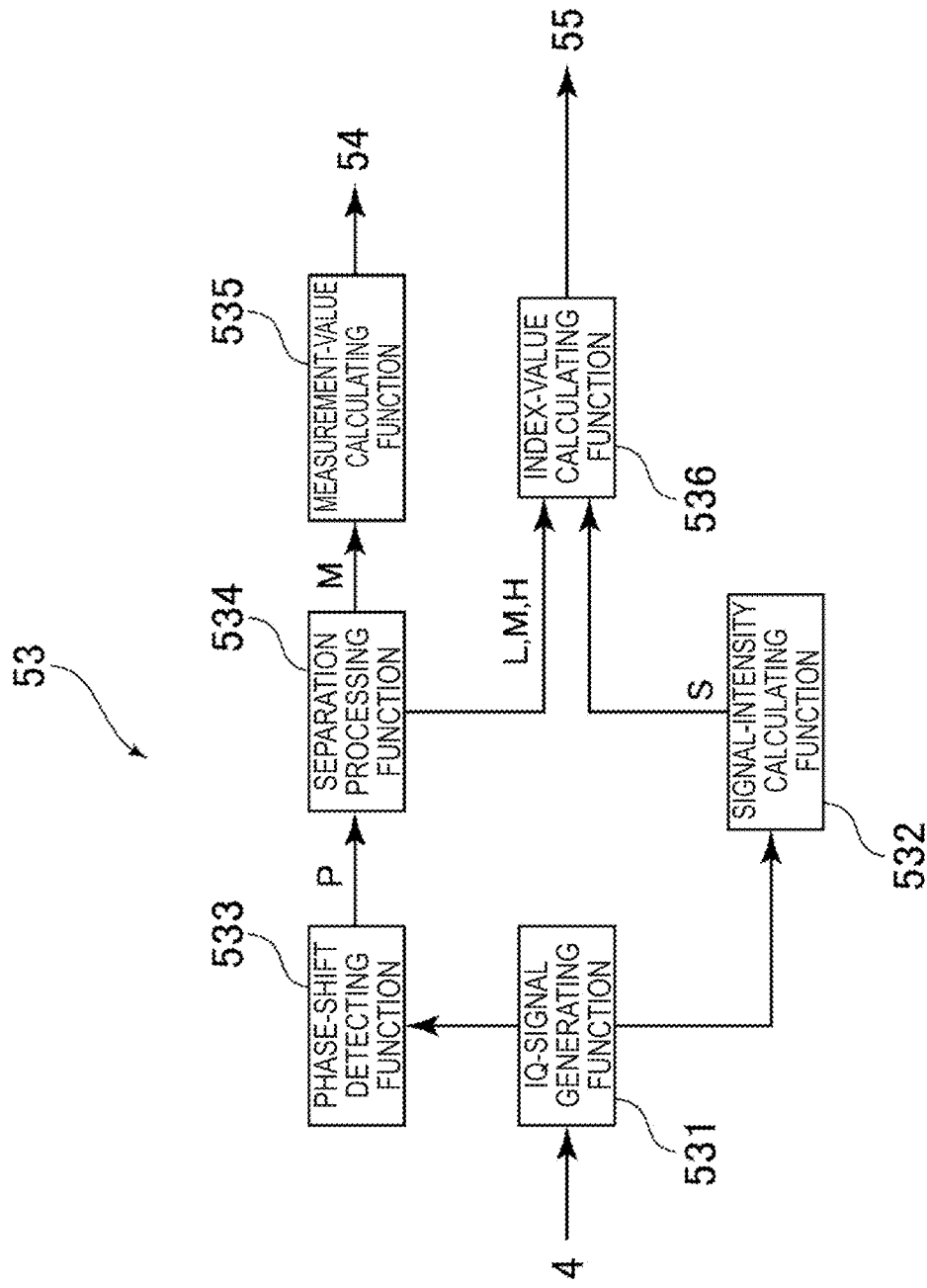
FIG. 12 A functional block diagram showing another example of details of the elasticity processing function.

Moreover, as shown in FIG. 11, the display processing function 55 may display the first bar BA1 to fourth bar BA4 without displaying the bar BA indicating the representative value Ir. In this case, the elasticity processing function 53 may have the representative-value calculating function 537 and index-value comparing function 538 or none of them as shown in FIG. 12. By the first bar BA1 to fourth bar BA4 being thus displayed without the bar BA being displayed, the factor that deteriorates reliability of the measurement value V can be known as described before.

Furthermore, the display processing function 55 may display by text a factor corresponding to each of all index values that are less than the threshold TH described above among the first index value I1 to fourth index value I4. In addition, the control circuit 5 may output by voice from the speaker 9 the factor corresponding to each of all index values that are less than the threshold TH described above among the first index value I1 to fourth index value I4. In this case, when the representative value Ir is less than the threshold TH, factors corresponding to all index values that are less than the threshold TH may be displayed by text or output by voice; or alternatively, the factors corresponding to all index values that are less than the threshold TH may be displayed by text or output by voice irrespective of whether or not the representative value Ir is less than the threshold.

Moreover, the embodiment in the preceding description may be a method of controlling an ultrasonic apparatus, said apparatus comprising:

an ultrasonic probe for performing transmission of ultrasonic push pulses to biological tissue in a subject to be examined, and transmission of ultrasonic detecting pulses for detecting shear waves generated by said push pulses in said biological tissue; and a control circuit, wherein said method of controlling comprises:

calculating a measurement value relating to elasticity of said biological tissue based on echo signals from said ultrasonic detecting pulses;

calculating an index value indicating a degree of reliability of said measurement value for each of a plurality of factors that deteriorate the reliability of said measurement value based on the echo signals from the ultrasonic detecting pulses; and notifying a factor corresponding to at least one index value for which said degree of reliability does not meet a required standard.

DESCRIPTION OF REFERENCE SYMBOLS

1 Ultrasonic diagnostic apparatus
2 Ultrasonic probe
5 Control circuit
6 Display device
9 Speaker
55 Display processing function
531 IQ-signal generating function
532 Signal-intensity calculating function
533 Phase-shift detecting function
534 Separation processing function
535 Measurement-value calculating function
536 Index-value calculating function
537 Representative-value calculating function
538 Index-value comparing function

The invention claimed is:

1. An ultrasonic apparatus comprising:
an ultrasonic probe for performing transmission of ultrasonic push pulses to biological tissue in a subject to be examined, and transmission of ultrasonic detecting pulses for detecting shear waves generated by said push pulses in said biological tissue; and
a control circuit, wherein said control circuit executes:
a measurement-value calculating function of calculating a measurement value relating to elasticity of said biological tissue based on echo signals from said ultrasonic detecting pulses;
an index-value calculating function of calculating an index value indicating a degree of reliability of said measurement value for each of a plurality of factors that deteriorate the reliability of said measurement value based on the echo signals from the ultrasonic detecting pulses; and
a notifying function of notifying a factor corresponding to at least one index value for which said degree of reliability does not meet a required standard.

2. The ultrasonic apparatus as recited in claim 1, wherein: said notifying function notifies a factor corresponding to each of all index values for which said required standard is not met.

3. The ultrasonic apparatus as recited in claim 1, wherein: in a case that there are a plurality of index values that do not meet said required standard, said notifying function notifies a factor corresponding to an index value that gives lowest reliability.

4. The ultrasonic apparatus as recited in claim 3, wherein: said control circuit further executes an index-value comparing function of comparing an index value calculated for each of said plurality of factors with another, and identifying an index value that gives lowest said reliability.

5. The ultrasonic apparatus as recited in claim 1, wherein: said required standard is a threshold-based standard determined for said index values.

6. The ultrasonic apparatus as recited in claim 5, wherein: said notifying function decides whether or not said degree of reliability meets the required standard with reference to said threshold to perform notification of said factor.

7. The ultrasonic apparatus as recited in claim 1, wherein: said control circuit further executes a representative-value calculating function of calculating, based on said plurality of index values, a representative value of the index values indicating the degrees of reliability of said measurement value, and
in a case that said degree of reliability of said representative value does not meet the required standard, said notifying function notifies a factor corresponding to at least one index value for which said degree of reliability does not meet the required standard.

8. The ultrasonic apparatus as recited in claim 1, wherein: said index-value calculating function detects, based on the echo signals from said ultrasonic detecting pulses, a temporal change of a displacement of said biological tissue caused by said shear waves, and calculates each of said plurality of index values based on at least one of said temporal change and signal intensity of said echo signals.

9. The ultrasonic apparatus as recited in claim 8, wherein: said control circuit further executes:
an IQ-signal generating function of generating IQ signals based on said echo signals;
a phase-shift detecting function of detecting a phase shift of said echo signals by applying autocorrelation processing to said IQ signals; and
a separation processing function of separating signals indicating said phase shift into a signal component in each of a plurality of frequency bands, and
said index-value calculating function uses at least one of said signal components for the detection of a temporal change of a displacement of said biological tissue.

10. The ultrasonic apparatus as recited in claim 8, wherein: said control circuit further executes:
an IQ-signal generating function of generating IQ signals based on said echo signals; and
a signal-intensity calculating function of calculating signal intensity of said IQ signals as signal intensity of said echo signals.

11. The ultrasonic apparatus as recited in claim 1, further comprising:
a display device, wherein
said notifying function is a function of notifying the factor corresponding to said at least one index value by displaying at least one of a figure and text on said display device.

12. The ultrasonic apparatus as recited in claim 7, further comprising:
a display device, wherein
said notifying function is a function of notifying the factor corresponding to said at least one index value by displaying at least one of a figure and text representing said representative value on said display device, and is a function of making said notification by displaying at least one of said figure and said text in a different display mode depending upon the factor corresponding to said at least one index value.

13. The ultrasonic apparatus as recited in claim 11, wherein: said notifying function displays at least one of said figure and text in a different color depending upon the factor corresponding to said at least one index value.

14. The ultrasonic apparatus as recited in claim 1, further comprising:
a speaker, wherein
said notifying function is a function of notifying the factor corresponding to said at least one index value by sound from said speaker.

15. The ultrasonic apparatus as recited in claim 1, wherein: said notifying function further notifies measures to eliminate the factor corresponding to said at least one index value.

16. The ultrasonic apparatus as recited in claim 1, wherein: said measurement-value calculating function detects said shear waves by detecting, based on the echo signals from said ultrasonic detecting pulses, the temporal change of the displacement of said biological tissue caused by said shear waves, and calculates a measurement value relating to elasticity of said biological tissue based on detected said shear waves.

17. The ultrasonic apparatus as recited in claim 1, comprising:
   a display device, wherein
   said measurement-value calculating function calculates said measurement values at a plurality of points in a required region of said biological tissue,
   said display device displays an elasticity image in said required region created based on said measurement values, and
   said index-value calculating function calculates said index value in said required region.

18. A program for controlling an ultrasonic apparatus, said apparatus comprising:
   an ultrasonic probe for performing transmission of ultrasonic push pulses to biological tissue in a subject to be examined, and transmission of ultrasonic detecting pulses for detecting shear waves generated by said push pulses in said biological tissue; and
   a control circuit, wherein said program for controlling the ultrasonic apparatus causes said control circuit to execute:
   a measurement-value calculating function of calculating a measurement value relating to elasticity of said biological tissue based on echo signals from said ultrasonic detecting pulses;
   an index-value calculating function of calculating an index value indicating a degree of reliability of said measurement value for each of a plurality of factors that deteriorate the reliability of said measurement value based on the echo signals from the ultrasonic detecting pulses; and
   a notifying function of notifying a factor corresponding to at least one index value for which said degree of reliability does not meet a required standard.

* * * * *